United States Patent

Shirahata et al.

Patent Number: 4,748,251
Date of Patent: May 31, 1988

[54] 7-N-AMINOMETHYLENEMITOMYCIN DERIVATIVE

[75] Inventors: Kunikatsu Shirahata, Komae; Motomichi Kono, Machida; Masaji Kasai, Fujisawa; Makoto Morimoto, Shizuoka; Tadashi Ashizawa, Numazu, all of Japan

[73] Assignee: Kyowa Hakko Kogyo Co., Ltd., Tokyo, Japan

[21] Appl. No.: 824,227

[22] Filed: Jan. 30, 1986

[30] Foreign Application Priority Data

Jan. 31, 1985 [JP] Japan .................. 60-17532

[51] Int. Cl.$^4$ ............... C07D 487/14; A61K 31/40
[52] U.S. Cl. .................................... 548/422
[58] Field of Search .................. 548/422; 514/410

[56] References Cited

U.S. PATENT DOCUMENTS

| 4,374,774 | 2/1983 | Kasai et al. | 548/422 |
| 4,395,558 | 7/1983 | Kasai et al. | 548/422 |
| 4,487,769 | 12/1984 | Vyas et al. | 514/410 X |
| 4,567,256 | 1/1986 | Vyas et al. | 548/422 X |

FOREIGN PATENT DOCUMENTS

| 0008021 | 2/1980 | European Pat. Off. |
| 0008807 | 12/1983 | France . |
| 0122797 | 9/1979 | Japan . |
| 0045322 | 3/1980 | Japan . |
| 2121796 | 1/1984 | United Kingdom . |

OTHER PUBLICATIONS

Merck Index, 10th Ed. (1983) 6079, 7466.
J.A.C.S., vol. 105 (1983) 7199:200.
J. Nat. Prod., vol. 42, No. 5 (1979) 549:68.
Abs. Lect. of 43d Spr. Ann. Meeting of Chem. Soc. Japan.
J. Med. Chem., vol. 24 (1981) 975:81.
J. Med. Chem., vol. 26 (1983) 16:20; 1453:7.
J. Med. Chem., vol. 27 (1984) 701:8.

Primary Examiner—Mark L. Berch
Assistant Examiner—William A. Teoli, Jr.
Attorney, Agent, or Firm—Fitzpatrick, Cella, Harper & Scinto

[57] ABSTRACT

Mitomycin derivatives represented by the formula (I):

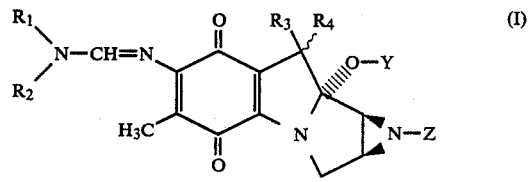

wherein $R_1$ and $R_2$ may be the same or different, and represent a hydrogen atom or a lower alkyl group; $R_3$ and $R_4$ mean that when $R_3$ is a hydrogen atom, $R_4$ represents —$CH_2OCONH_2$ or

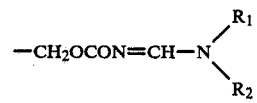

(wherein $R_1$ and $R_2$ have the same significances as defined above), or $R_3$ and $R_4$ are combined to form =$CH_2$; Y and Z may be the same or different, and represent a hydrogen atom or a methyl group; ～～ represents α- or β-bond, provided that Y represents a hydrogen atom when $R_4$ takes β-configuration, have an excellent antitumor activity.

1 Claim, No Drawings

7-N-AMINOMETHYLENEMITOMYCIN DERIVATIVE

BACKGROUND OF THE INVENTION

The present invention relates to novel mitomycin derivatives showing antibacterial and anti-tumor activities, a process for production thereof and an anti-tumor composition containing the same.

Mitomycins are generally known as antibiotics showing antibacterial and anti-tumor activities. Representative mitomycins include mitomycin A, mitomycin B, mitomycin C and porfiromycin, which are described in Merck Index, 10th edition; mitomycin D and mitomycin E, which are described in Japanese Published Unexamined Patent Application No. 122797/79; mitomycin F, which is described in Japanese Published Unexamined Patent Application No. 45322/80; etc. These mitomycins can be isolated from culture liquor of *Streptomyces caespitosus*. Further, 9-epi-mitomycin B and 9-epi-mitomycin D are chemically derived from mitomycin B (U.S. Pat. No. 4,395,558). Recently, the absolute configuration of mitomycin has been corrected [J. Am. Chem. Soc., 105, 7199 (1983)]. Structures of various mitomycins mentioned above corrected according thereto are shown by formulae A and B (the same shall apply to formula C).

Formula A: Main mitomycins obtained from natural source

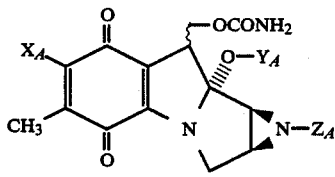

| Mitomycin | $X_A$ | $Y_A$ | $Z_A$ | C-9 |
|---|---|---|---|---|
| A | $OCH_3$ | $CH_3$ | H | $\beta$ |
| B | $OCH_3$ | H | $CH_3$ | $\alpha$ |
| C | $NH_2$ | $CH_3$ | H | $\beta$ |
| D | $NH_2$ | H | $CH_3$ | $\alpha$ |
| E | $NH_2$ | $CH_3$ | $CH_3$ | $\alpha$ |
| F | $OCH_3$ | $CH_3$ | $CH_3$ | $\beta$ |
| J | $OCH_3$ | $CH_3$ | $CH_3$ | $\alpha$ |
| Porfiromycin | $NH_2$ | $CH_3$ | $CH_3$ | $\beta$ |

Formula B: 9$\beta$-Mitomycins having hydroxy group at the 9a-position

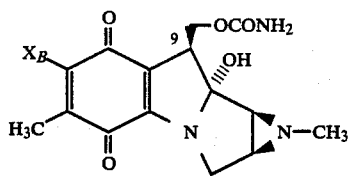

| 9-epi-mitomycin B | $X_B = OCH_3$ |
| 9-epi-mitomycin D | $X_B = NH_2$ |

In addition, mitomycins having a double bond at the 9- and 10-positions are also known. Processes for producing them are disclosed in EP 0008021A1. The structure of a double bond type mitomycin is shown by formula C.

Formula C: Double bond type mitomycin

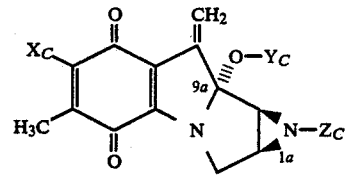

| | $X_C$ | $Y_C$ | $Z_C$ |
|---|---|---|---|
| Mitomycin H | $OCH_3$ | H | $CH_3$ |
| Mitomycin G | $NH_2$ | $CH_3$ | $CH_3$ |
| Mitomycin K | $OCH_3$ | $CH_3$ | $CH_3$ |
| 9a-O—Demethylmitomycin G | $NH_2$ | H | $CH_3$ |
| 1a-Demethylmitomycin G | $NH_2$ | $CH_3$ | H |
| 1a-Demethylmitomycin K | $OCH_3$ | $CH_3$ | H |

Mitomycins exhibit excellent anti-tumor activity, but they cause side effects such as decrease of leucocytes, etc. on the other hand. Therefore, for the purpose of increasing the activity or reducing the toxicity, a large number of derivatives have been synthesized and their biological properties have been investigated.

Among these mitomycin derivatives, examples of compounds containing a modified amino group at the 7-position, which are relevant to the present invention, include those reported in J. Med. Chem., 24, 975 (1981), J. Med. Chem., 26, 16 (1983), J. Med. Chem., 26, 1453 (1983), J. Med. Chem., 27, 701 (1984), etc. It is also reported in these publications that mitomycin derivatives having a modified amino group at the 7-position exhibit an anti-tumor activity in vivo. Among the mitomycin derivatives having a modified amino group at the 7-position, examples of compounds which are especially relevant to the present invention are disclosed in GB 2121796A. It is reported that inter alia, 7-(dimethylaminomethylene)amino-9a-methoxymitosane (hereinafter referred to as Compound A) disclosed in Example 8 of the patent application possesses a particularly excellent anti-tumor activity. However, the compounds of the patent application are obtained using as starting materials mitomycin A, mitomycin C, porfiromycin and 7-N-methylmitomycin C and thus limited to compounds that have the same configuration as that of mitomycin C (cf. GB 2121796A).

On the other hand, the mitomycin derivatives having an anti-tumor activity which are covered by the present invention are shown by the following formulae (I-1), (I-2) and (I-3):

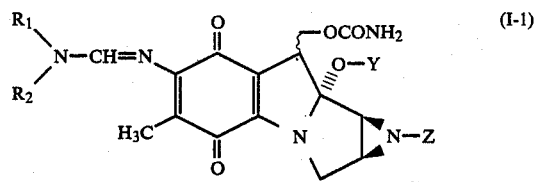

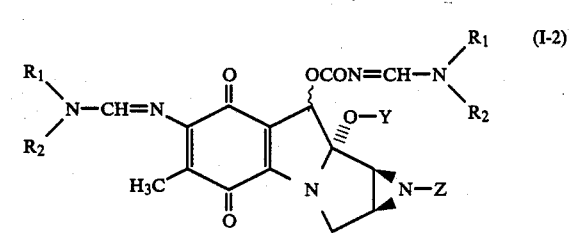

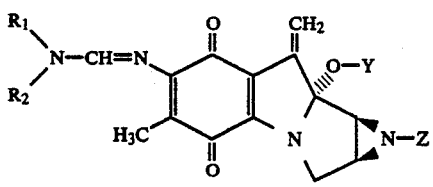

wherein $R_1$ and $R_2$ represent a hydrogen atom or a lower alkyl group; Y and Z represent a hydrogen atom or a methyl group; and ⁓⁓⁓ represents α- or β-bond, provided that Y represents a hydrogen atom when the substituent at the 9-position takes β-configuration.

The compound shown by formula (I-1) [hereinafter referred to as Compound (I-1); and compounds of other formula numbers are likewise referred to] is synthesized using mitomycin B or its analogues as starting compounds when the substituent at the 9-position take α-configuration. Examples of the analogues include mitomycin D and mitomycin E which have an amino group at the 7-position. These derivatives are obtained from nature as extremely minor components in the fermentation of mitomycin C (Japanese Published Unexamined Patent Application No. 122797/79), and are difficult to obtain unless they are chemically derived from mitomycin B.

Mitomycin B is also a compound isolated as a minor component in the fermentation of mitomycin C and, it has thus been considered to be difficult to obtain an amount usable as a starting compound in chemical synthesis. However, co-researchers of the present inventors have investigated in detail culture conditions for the fermentation of mitomycin C and a method for isolation and purification of mitomycin B with an attempt to produce an improved amount of mitomycin B and succeeded in greatly improving productivity of mitomycin B. As a result, it has become possible to produce mitomycin B in large amounts at a low cost. Thus, the present invention which utilizes mitomycin B as a starting compound has come to be of industrial value.

On the other hand, the compounds whose substituent at the 9-position takes β-configuration belong to generally well known mitomycins. A representative is mitomycin C. However, all the mitomycins obtained from nature whose substituent at the 9-position takes β-configuration have a methoxy group at the 9a-position. Mitomycins having the same configuration as that of mitomycin C, namely, taking 9-β configuration and having 9a-OH (cf. formula A) are generally difficult to obtain. 9-Epi-mitomycin D relevant to the present invention is a special compound that can be obtained using mitomycin B as a starting compound. Thus, the compounds which are covered by the present invention are extremely characteristic in chemical structure and are hardly obtainable even to one skilled in the art, although they may be collectively referred to as mitomycins. Such a background is also the case with the double bond type mitomycin [Compound (I-3)]. In addition, it has been proved by experiments that some compounds of the present invention exhibit superior anti-tumor activity against leukemia P-388 to Compound A (shown in Reference Example) described in GB 2121796A (later described). The present invention is thus obviously characteristic as compared to the prior art.

As is evident from the publications referred to hereinabove, a large number of mitomycin derivatives have already been synthesized, but development of more excellent anti-tumor agents has still been desired in view of enhancement of anti-tumor activity or reduction of toxicity. During the course of extensive investigations for purposes of producing substances having such properties, the present inventors have also synthesized Compound A independently from GB 2121796A, and noted its excellent anti-tumor activity. As a result of further investigations on production of mitomycin derivatives having a more excellent antibacterial activity and anti-tumor activity with reduced toxicity, the present inventors have found the compounds having biochemical properties superior to those of Compound A and have accomplished the present invention.

SUMMARY OF THE INVENTION

The present invention relates to mitomycin derivatives represented by formula (I):

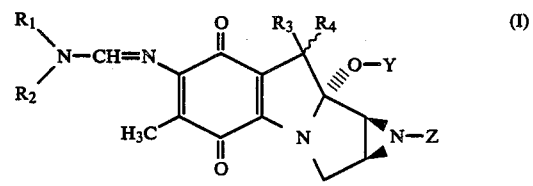

[wherein $R_1$ and $R_2$ may be the same or different, and represent a hydrogen atom or a lower alkyl group; $R_3$ and $R_4$ mean that when $R_3$ is a hydrogen atom, $R_4$ represents —$CH_2OCONH_2$ or $$-CH_2OCON=CH-N\begin{matrix}R_1\\ \\R_2\end{matrix}$$

(wherein $R_1$ and $R_2$ have the same significances as defined above), or $R_3$ and $R_4$ are combined to represent =$CH_2$; Y and Z may be the same or different, and represent a hydrogen atom or a methyl group; and ⁓⁓⁓ represents α- or β-bond, provided that Y represents a hydrogen atom when $R_4$ takes β-configuration], a process for production thereof and an anti-tumor composition containing the same. Compound (I) consists of Compounds (I-1), (I-2) and (I-3).

DETAILED DESCRIPTION OF THE INVENTION

In the definition of $R_1$ and $R_2$ in formula (I), the lower alkyl group includes a straight or branched chain alkyl group having 1 to 5 carbon atoms, for example, methyl, ethyl, i-propyl, etc.

Reaction schemes for obtaining Compound (I-1) are shown below.

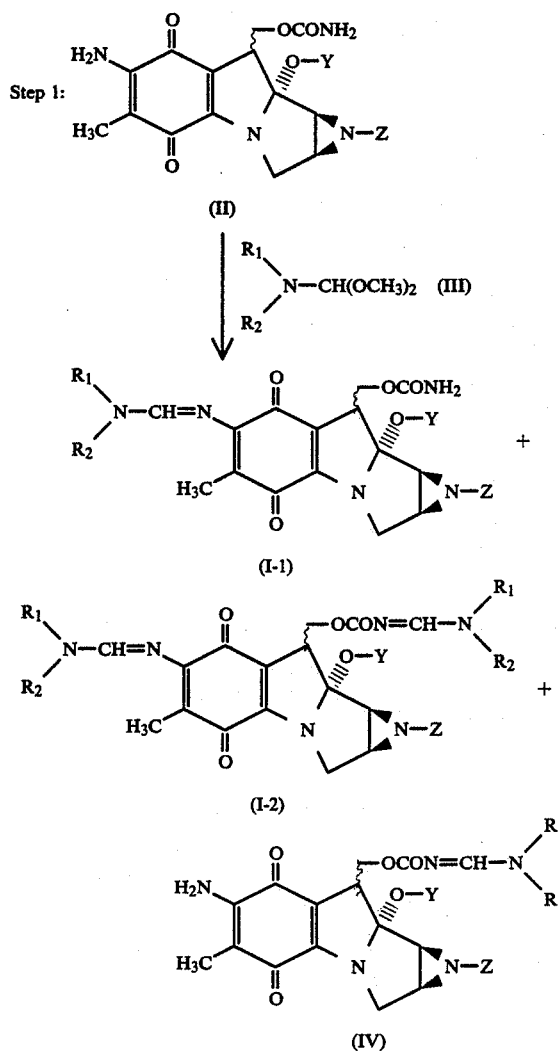

Step 2: (I-2) ⟶ (I-1)

Step 3: (IV) + (III) ⟶ (I-2)

Compound (I) can be prepared by reacting Compound (II) with Compound (III) in an inert solvent. In this case, Compounds (I-2) and (IV) are formed as by-products. Compound (I-2) can be converted to Compound (I-1) by selective solvolysis of —OCON═CH—N($R_1$)($R_2$) at the 10-position (Step 2). Compound (IV) can be converted to Compound (I-2) by reacting with Compound (III) under conditions similar to Step 1 to form Compound (I-2) (Step 3) and subsequently subjecting Compound (I-2) to the above treatment. As the solvent in Step 1, chloroform, dichloromethane, diethyl ether, tetrahydrofuran, dioxane, ethylene glycol dimethyl ether, acetonitrile, dimethylsulfoxide, dimethylformamide, etc. may be used singly or in combination. Though reaction temperature and reaction time vary depending upon Compound (IV) and the concentration of reactants, it is generally sufficient to conduct the reaction at −30° to 70° C. for around fifty minutes to several hours.

As the solvent used in Step 2, lower alcohols such as methanol, ethanol, propanol, etc. are suitable. They may be used singly or as a mixture with an ether, acetonitrile, dimethylsulfoxide, dimethylformamide, etc. The reaction is carried out generally at a temperature of −30° to 70° C. for around fifty minutes to several hours. As the catalyst, weak inorganic bases may be used, but weakly basic amines having a large steric hindrance are preferred. Examples of the latter include aminodiphenylmethane, tertiary butyl amine, etc. Such solvolysis of dialkylaminomethyleneimine groups is also described in GB 2121796A.

Compound (I-1) may also be synthesized through the following reaction scheme using Compound (V) which is disclosed in EP 0008021A1 as a starting compound.

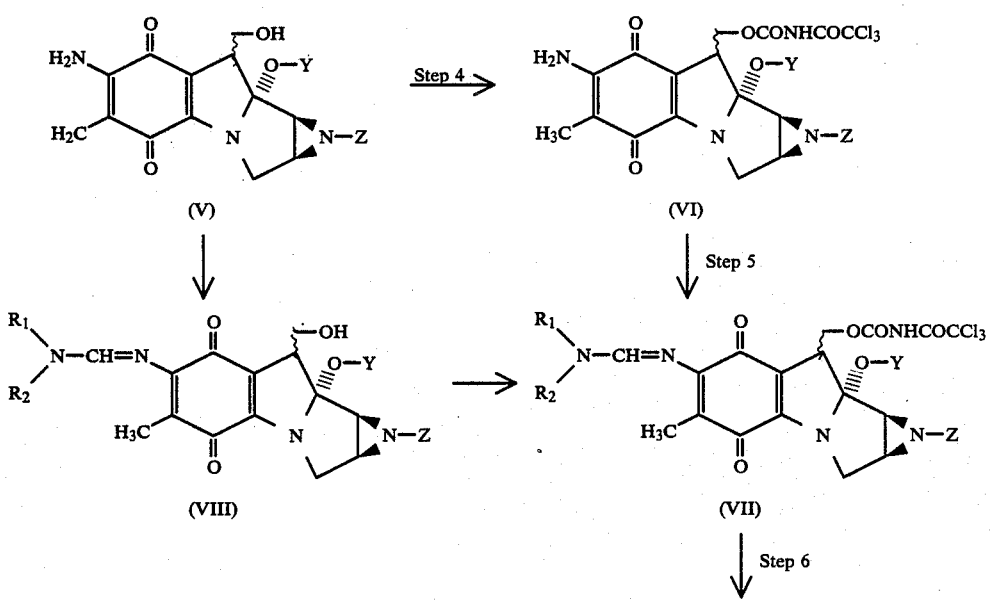

-continued

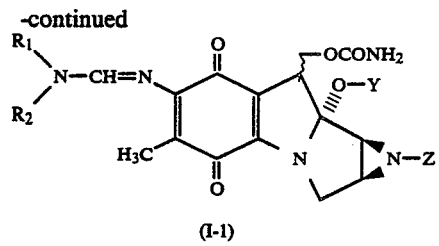

(I-1)

Namely, Compound (V) is reacted with trichloroacetyl isocyanate to produce Compound (VI) (Step 4). Then, Compound (III) is reacted with Compound (VI) in a manner similar to Step 1 to obtain Compound (VII) (Step 5). Compound (VII) may also be synthesized by first reacting Compound (V) with Compound (III) and then reacting the resulting Compound (VIII) with trichloroacetyl isocyanate. By solvolysis of the thus obtained Compound (VII), Compound (I-1) can be obtained (Step 6). The trichloroacetylcarbamoylation in Step 4 and the reaction for forming the carbamoyl group in Step 6 can be carried out in a conventional manner (J. Natural Product, 42, 549 (1979) and Abstract of Lectures of 43rd Spring Annual Meeting of the Chemical Society of Japan in Tokyo, distributed in advance, page 910, 1981). As the solvent to be used in Step 4, chloroform, dichloromethane, diethyl ether, tetrahydrofuran, dioxane, ethylene glycol dimethyl ether, benzene, toluene, etc. are suitable. These solvents may be used singly or in combination. The reaction is carried out generally at $-30°$ to $30°$ C. for around fifty minutes to several hours. As the catalyst to be used in Step 6, inorganic salts such as carbonates, bicarbonates, etc. of alkali metal or alkaline earth metal; amines such as triethylamine, diisopropylethylamine, pyrrolidine, piperidine, etc. are suitable. The reaction is carried out generally at $-30°$ to $70°$ C. for around fifty minutes to around fifty hours. The reaction in Step 5 is carried out in a manner similar to Step 1 described above.

Next, the process for producing Compound (I-3) is explained.

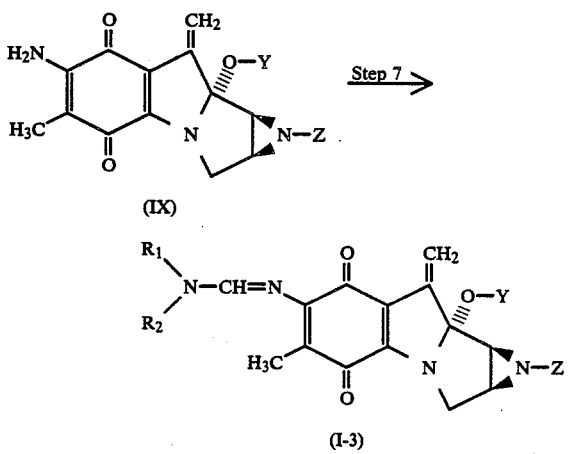

Compound (I-3) can be produced by reacting Compound (IX) with Compound (III) in an inert solvent. The reaction in this step can be carried out in a manner similar to Step 1 described above.

According to a further feature of the present invention, there are provided pharmaceutical compositions containing as an active ingredient at least one mitomycin derivative of formula (I) or a pharmacologically acceptable salt thereof in association with one or more pharmaceutical carriers and/or excipients.

For use as, for example, anti-tumor agents for mammals including human beings, Compound (I) may be dissolved, for example, in physiological saline solution, or a glucose, lactose or mannitol injection solution. Administration may be effected, for example, by intravenous injection at a dose of 0.005–10 mg/kg of body weight for one day. Compound (I) may be freeze-dried in accordance with the Pharmacopoeia of Japan and a dry powder injectable formulation may be prepared with addition of sodium chloride. The anti-tumor agent may further contain well-known pharmacologically acceptable diluent(s), adjuvant(s) and/or carrier(s) such as salts which fulfil pharmaceutical utility. The dose of a pharmaceutical composition according to the invention may be varied depending upon, for example, the age and symptoms of each patient. The administration schedule may be varied depending upon the dose. Thus, administration may be effected, for example, once a week or once a three weeks. If desired, oral administration is also possible, e.g. using the above doses, for which purpose tablets, powders, granules, etc. containing appropriate excipients may be used. If desired, intra-arterial, intraperitoneal and intrapleural administrations may also be used.

Certain specific embodiments of the present invention are illustrated by the following examples. Physico-chemical data of each compound was obtained by using the following devices.

$^1$H-NMR: JEOL FX-100 Spectrometer.
MS: Hitachi M-80B Mass Spectrometer.
IR: Shimadzu IR-27-G and JASCO IR 810.
Silica gel TLC: Merck Art 5714.

EXAMPLE 1

9a-O-Demethyl-7-N-dimethylaminomethylenemitomycin G (Compound 1)

To 1 ml of dry dimethylformamide (hereinafter referred to as DMF) are added 0.1 ml of dimethylformamide dimethylacetal (hereinafter referred to as DMFA) and 90 mg of 9a-O-demethylmitomycin G. The mixture is stirred at room temperature for 6 hours in a nitrogen stream.

After the solvent is removed by distillation under reduced pressure, the product is separated by silica gel column chromatography using CHCl$_3$-MeOH (98:2 v/v) as a developing solvent. Then, the product is subjected to silica gel column chromatography again for purification. The solution eluted with AcOEt—MeOH (99:1 v/v) is concentrated under reduced pressure to isolate a dark green pasty substance. The substance is dissolved in a small amount of CHCl$_3$, and the solution is dropwise added to cyclohexane, whereby Compound 1 is precipitated as a green precipitate. The precipitate is separated by filtration to obtain 81 mg of Compound 1. Yield: 75%.

$^1$H-NMR (CDCl$_3$): δ1.86(3H, s), 2.19(3H, s), 2.26(2H, m), 3.03(3H, s), 3.07(3H, s), 3.48(1H, dd, J=12.7, 1.3), 4.17(1H, d, J=12.7), 5.44(1H, d, J=0.5), 6.03(1H, d, J=0.5), 7.64(1H, s).

IR (KBr): 3400, 2928, 2854, 1644, 1620, 1529, 1376, 1306, 1113, 1054 cm$^{-1}$.

MS (m/z): 328(M+), 311, 284, 259.

High resolution MS: M+=328.1517 (calcd. for C$_{17}$H$_{20}$N$_4$O$_3$=328.1533). TLC (CHCl$_3$—MeOH, 19:1 v/v): Rf=0.40.

EXAMPLE 2

1a-Demethyl-7-N-dimethylaminoethylenemitomycin G (Compound 2)

The same procedure as in Example 1 is repeated except that 53 mg of 1a-demethylmitomycin G is used as a starting compound, whereby 47 mg of Compound 2 is obtained as a green powder. Yield: 74%.

$^1$H-NMR (CDCl$_3$): δ1.95(3H, s), 2.85(2H, br.s), 3.05(3H, s), 3.10(3H, s), 3.11(3H, s), 3.55(1H, br.d, J=12.9), 4.27(1H, d, J=12.9), 5.42(1H, d, J=0.6), 6.22(1H, d, J=0.6), 7.74(1H, s).

IR (KBr): 3292, 2930, 2854, 1645, 1622, 1599, 1572, 1532, 1435, 1376, 1304, 1254, 1214, 1111, 1083, 1053, 939 cm$^{-1}$.

MS (m/z): 328(M+), 313, 297, 282, 254.

High resolution MS: M+=328.1532 (calcd. for C$_{17}$H$_{20}$N$_4$O$_3$=328.1534).

TLC (CHCl$_3$—MeOH, 19:1 v/v): Rf=0.48.

EXAMPLE 3

7-N-Dimethylaminomethylenemitomycin D (Compound 3a) and

7-N,N$^{10}$-bis(dimethylaminomethylene)mitomycin D (Compound 3b) (in the nomenclature of the compound, N$^{10}$ refers to the nitrogen atom in the carbamoyloxy group at the 10-position of mitomycin; the same rule is applied hereinafter)

In 0.4 ml of dry DMF containing 80 μl of DMFA is dissolved 83 mg of mitomycin D. The solution is stirred at room temperature for 40 minutes in a nitrogen stream.

After the solvent is removed by distillation under reduced pressure, the residue is subjected to silica gel column chromatography. A green fraction (called Fraction A) eluted with CHCl$_3$—MeOH (95:5 v/v) is obtained. Subsequently, the system is developed with CHCl$_3$—MeOH (93:7 v/v) and another green fraction (called Fraction B) is obtained. Finally, the solvent is changed to CHCl$_3$—MeOH (85:15 v/v) and the obtained fractions are collected, from which 26 mg of mitomycin D is recovered.

After Fraction B is concentrated, the concentrate is subjected to silica gel column chromatography again for purification. Green fractions eluted with AcOEt—MeOH (92:8 v/v) are collected and concentrated to obtain 25 mg of compound 3a as a dark green powder. Yield: 38%.

$^1$H-NMR (CDCl$_3$): δ1.90(3H, s), 2.25(5H, s), 3.03(3H, s), 3.08(3H, s), 3.46(1H, br.d, J=12.7), 3.71(1H, t, J=4.2), 4.08(1H, d, J=12.7), 4.20(1H, br.), 4.70(2H, d, J=4.2), 4.72(2H, br.s), 7.70(1H, s).

IR (KBr): 3430, 2930, 1703, 1621, 1535, 1310 cm$^{-1}$.

MS (m/z): 389(M+), 371, 346, 328, 310, 295, 273, 259.

High resolution MS: M+=389.1694 (calcd. for C$_{18}$H$_{23}$N$_5$O$_5$=389.1697).

TLC (CHCl$_3$—MeOH, 19:1 v/v): Rf=0.17.

After Fraction A is concentrated, the residue is further purified by means of preparative silica gel thin layer chromatography. The system is developed with AcOEt—MeOH (19:1 v/v) and green bands showing Rf=0.09 are collected, whereby 26 mg of Compound 3b is obtained as a dark green powder. Yield: 34%.

$^1$H-NMR (CDCl$_3$): δ1.90(3H, s), 2.25(3H, s), 2.28(2H, m), 3.03(3H, s), 3.05(3H, s), 3.07(3H, s), 3.11 (3H, s), 3.48(1H, dd, J=12.7, 1.7), 3.78(1H, m), 4.08(1H, d, J=12.7), 4.51(1H, br.), 4.75(2H, m), 7.70(1H, s), 8.38(1H, s).

IR (KBr): 3380, 2920, 1617, 1526, 1419, 1374, 1309, 1263, 1226, 1113, 1076, 1059 cm$^{-1}$.

MS (m/z): 444 (M+, calcd. for C$_{21}$H$_{28}$N$_6$O$_5$=444), 426, 328.

TLC (CHCl$_3$—MeOH, 19:1 v/v): Rf=0.29.

EXAMPLE 4

7-N-Dimethylaminomethylenemitomycin E (Compound 4a) and

7-N,N$^{10}$-bis(dimethylaminomethylene)mitomycin E (Compound 4b)

In 0.4 ml of dry DMF containing 80 μl of DMFA is dissolved 39 mg of mitomycin E. The solution is stirred at room temperature for 1 hour and 20 minutes in a nitrogen stream. After the solvent is removed by distillation under reduced pressure, the residue is subjected to column chromatography using as an eluting solvent CHCl$_3$—MeOH (97:3 v/v) to obtain a green fraction (called Fraction A). By subsequent elution with CHCl$_3$—MeOH (92:8 v/v), a blue fraction (called Fraction B) is obtained. Fraction B is concentrated and the residue is purified by means of silica gel thin layer chromatography, whereby 15 mg of mitomycin E is recovered.

Fraction A is concentrated, and the concentrate is subjected to silica gel thin layer chromatography followed by development with AcOEt—MeOH (19:1 v/v). From green bands showing Rf=0.16, 7 mg of Compound 4a (yield 25%) is isolated as a dark green powder, and 4 mg of Compound 4b (yield 13%) is isolated from green bands showing Rf=0.02 as a dark green powder.

Compound 4a:

$^1$H-NMR (CDCl$_3$): δ1.91(3H, s), 2.20(1H, d, J=4.6), 2.31(3H, s), 2.36(1H, dd, J=4.6, 2.0), 3.03(3H, s), 3.07(3H, s), 3.31(3H, s), 3.56(1H, dd, J=12.7, 2.0), 3.84(1H, dd, J=9.5, 3.9), 3.95(1H, d, J=12.7), 4.43(1H, dd, J=10.7, 9.5), 4.61(2H, br.s), 4.84(1H, dd, J=10.7, 3.9), 7.68(1H, s).

IR (KBr): 3450, 3362, 2922, 1713, 1625, 1548, 1538, 1326, 1304, 1117, 1074, 1051 cm$^{-1}$.

MS (m/z): 403(M+), 372, 342, 327, 311, 295.

High resolution MS: M+=403.1871 (calcd. for C$_{19}$H$_{25}$N$_5$O$_5$=403.1854).

Compound 4b:

$^1$H-NMR (CDCl$_3$): δ1.91(3H, s), 2.31(3H, s), 2.33(2H, m), 3.02(3H, s), 3.06(3H, s), 3.09(3H, s), 3.11(3H, s), 3.30(3H, s), 3.55(1H, br.d, J=12.2), 3.96(1H, d, J=12.2), 3.99(1H, dd, J=10.4, 4.3), 4.57(1H, dd, J=10.7, 10.4), 4.84(1H, dd, J=10.7, 4.3), 7.68(1H, s), 8.48(1H, s).

IR (KBr): 3450, 2920, 1624, 1544, 1306, 1115 cm$^{-1}$.

MS (m/z): 458(M+), 426, 400, 342.

High resolution MS: M+=458.2186 (calcd. for $C_{22}H_{30}N_6O_5$=458.2275).

EXAMPLE 5

Compound 4a

To 3 ml of a methanol solution containing 186 mg of Compound 4b is added 0.1 ml of diphenylaminomethane. The mixture is stirred at 55° C. for 2 hours in a nitrogen stream. After the solvent is removed by distillation under reduced pressure, the residue is subjected to silica gel column chromatography.

Elution is carried out initially with $CHCl_3$—MeOH (19:5 v/v), and then the proportion of MeOH in the eluting solvent is gradually increased. Green fractions eluted with 9:1 v/v are collected, and are further purified by means of silica gel chromatography using AcOEt—MeOH. In this chromatography, the initial proportion of both solvents is 95:5 and then the ratio of MeOH is gradually increased. Compound 4a is eluted with 93:7 v/v. The fractions are concentrated to obtain 14 mg of a dark green powder. Yield: 9%.

EXAMPLE 6

6-1) 9-Epi-$N^{10}$-trichloroacetylmitomycin D (Compound 6a) and $N^{10}$-trichloroacetylmitomycin D (Compound 6b)

In 110 ml of dry methylene chloride-chloroform (10:1 v/v) is dissolved 410 mg of unpurified 9-epi-10-decarbamoyl mitomycin D ( a process for production of this compound is described in U.S. Pat. No. 4,395,558, Example 1) containing about 10% of 10-decarbamoylmitomycin D. While the solution is stirred under ice cooling, 175 μl of trichloroacetyl isocyanate is added thereto. Twenty minutes after, 40 ml of tetrahydrofuran and 500 μl of trichloroacetyl isocyanate are added to the mixture, followed by stirring for further 2 hours. After 10 ml of methanol is added thereto, the solvent is removed by distillation under reduced pressure. The residue is subjected to silica gel column chromatography using chloroform-acetone (3:2 v/v). Blue fractions first eluted are collected, concentrated and dried to obtain 293 mg of Compound 6a as a dark brown solid.

$^1$H-NMR (py-$d_5$): δ1.98(3H, s), 2.19(3H, s), 2.19(1H, m), 2.58(1H, d, J=4.9), 3.63(1H, dd, J=12.7, 2.0), 4.01(1H, dd, J=11.2, 4.4), 4.50(1H, d, J=12.7), 4.86(1H, dd, J=11.2, 10.7), 5.44(1H, dd, J=10.7, 4.4), 8.47(1H, s).

IR (KBr): 3340, 2940, 1795, 1737, 1597, 1534, 1447, 1352, 1185, 847 cm$^{-1}$.

TLC ($CHCl_3$-acetone, 1:1 v/v): Rf=0.50.

Blue fractions eluted after Compound 6a in the above column chromatography are concentrated to obtain 22 mg of $N^{10}$-trichloroacetylmitomycin D (6b) as a dark brown solid.

$^1$H-NMR (py-$d_5$): δ1.97(3H, s), 2.07(3H, s), 2.17(1H, dd, J=4.6, 1.5), 2.26(1H, d, J=4.6), 3.60(1H, dd, J=12.7, 1.5), 4.13(1H, dd, J=9.5, 4.2), 4.42(1H, d, J=12.7), 5.29(1H, dd, J=10.5, 9.5), 5.47(1H, dd, J=10.5, 4.2), 7.53(2H, br.), 9.58(1H, br.).

TLC ($CHCl_3$-acetone, 1:1 v/v): Rf=0.42.

6-2) 9-Epi-7-N-dimethylaminomethylenemitomycin D (Compound 6c) and 9-epi-7-N-dimethylaminomethylene-$N^{10}$-trichloroacetylmitomycin D (Compound 6d)

In 2 ml of DMFA-DMF (1:4 v/v) is dissolved 100 mg of Compound 6a. The solution is stirred at room temperature for 4 hours in a nitrogen stream and then allowed to stand in a refrigerator at about 8° C. overnight. After the reaction mixture is concentrated under reduced pressure, the residue is subjected to silica gel column chromatography using $CHCl_3$—MeOH (97:3 v/v) and eluted green fractions, which are referred to as Fraction A hereinafter are collected. Elution is continued with $CHCl_3$—MeOH (92:8 v/v), whereby green fractions, which are referred to as Fraction B hereinafter, are obtained.

Fraction B is concentrated to obtain 13 mg of Compound 6c as a dark green solid. Yield: 16%.

$^1$H-NMR (py-$d_5$): δ2.16(3H, s), 2.21(1H, dd, J=4.6, 2.2), 2.30(3H, s), 2.73(1H, d, J=4.6), 2.80(3H, s), 2.84(3H, s), 3.66(1H, dd, J=12.7, 2.2), 4.16(1H, dd, J=11.5, 4.4), 4.45(H, d, J=12.7), 4.89(1H, dd, J=11.5, 10.5), 5.47(1H, dd, J=10.5, 4.4), 7.63(2H, br.s), 7.80(1H, s), 8.30(1H, br.s).

IR (KBr): 3430, 2918, 1709, 1630, 1543, 1307, 1059 cm$^{-1}$.

MS (m/z): 389 (M+, calcd. for $C_{18}H_{23}N_5O_5$=389), 371, 346, 328, 295.

TLC ($CHCl_3$—MeOH, 9:1 v/v): Rf=0.33.

Fraction A is concentrated to obtain 40.3 mg of Compound 6d as a dark green solid. Yield: 36%.

It is clear that the compound obtained from Fraction A is Compound 6d from the following fact.

In 1 ml of methanol is dissolved 40.3 mg of the solid obtained from Fraction A, and 4 mg of $K_2CO_3$ is added to the solution. The mixture is stirred at room temperature for 80 minutes. To the reaction solution is added 9 ml of $CHCl_3$. The mixture is subjected to silica gel column chromatography using a short column and elution is conducted with $CHCl_3$—MeOH (9:1 v/v). The eluate is concentrated under reduced pressure and the residue is again subjected to silica gel column chromatography using $CHCl_3$—MeOH (92.8 v/v). Eluted fractions of green bands are concentrated under reduced pressure. A small amount of n-hexane is added to the residue, and then the solvent is removed again by distillation under reduced pressure. The residue is dried to obtain 13.8 mg of a dark green powder. The physicochemical properties of this substance are identical with those of Compound 6c described above. Yield: 47%.

EXAMPLE 7

Antibacterial activities of some compounds covered by the present invention against various bacteria are shown by the minimum growth inhibitory concentration (μg/ml) in Table 1. The minimum growth inhibitory concentration was measured at pH 7.0 according to the agar dilution method. In the table, bacteria are indicated by the following letters.

SF: *Streptococcus faecalis* ATCC 10541
SA: *Staphylococcus aureus* ATCC 6538P
BS: *Bacillus subtilis* 10707
PV: *Proteus vulgaris* ATCC 6897
SS: *Shigella sonnei* ATCC 9290
KP: *Klebsiella pneumoniae* ATCC 10031

Further, MM-C in the table refers to mitomycin C.

TABLE 1

| | Antibacterial activity (minimum growth inhibitory concentration, μg/ml) | | | | | |
|---|---|---|---|---|---|---|
| Compound | SF | SA | BS | PV | SS | KP |
| 3a | 5.0 | 10 | 2.5 | 20 | >20 | 2.5 |
| 4a | 0.63 | 0.63 | 0.16 | 20 | 10 | 2.5 |
| 6c | 1.3 | 2.5 | 0.63 | 5.0 | 40 | 0.63 |
| 4b | 5 | 10 | 2.5 | — | — | 40 |

TABLE 1-continued

| Compound | Antibacterial activity (minimum growth inhibitory concentration, μg/ml) | | | | | |
|---|---|---|---|---|---|---|
| | SF | SA | BS | PV | SS | KP |
| 1 | 0.078 | 0.078 | 0.078 | 10 | 10 | 10 |
| 2 | 1.3 | 0.31 | 0.078 | 10 | 20 | 10 |
| MM-C | 0.31 | 0.16 | 0.04 | 0.08 | 2.5 | 0.04 |

EXAMPLE 8

Anti-tumor activity against Sarcoma 180 solid tumor and toxicity

Taking some of the compounds falling within the present invention as examples, anti-tumor activity ($ED_{50}$) against Sarcoma 180 solid tumor and acute toxicity ($LD_{50}$) as well as effect on peripheral leucocytes number ($WBC_{4000}$) are shown in Table 2.

$WBC_{4000}$ indicates the dose of a substance which reduces the peripheral leucocytes number to $4000/mm^3$.

TABLE 2

| Compound | $LD_{50}$ (mg/kg) | $ED_{50}$ (mg/kg) | $WBC_{4000}$ (mg/kg) |
|---|---|---|---|
| 3a | 8.3 | 3.9 | 4.3 |
| 6c | 9.4 | 14.0 | 11.2 |
| 3b | 26.3 | 20.9 | 18.7 |

The experiments were performed according to the following procedures.

(1) Effect against Sarcoma 180 solid tumor cells:

$5\times10^6$ cells of Sarcoma 180 solid tumor were implanted into ddY mice. 7 days later, ascites cells were sampled. The cells were washed once with a sterilized physiological solution of sodium chloride and were used to prepare a cell supspension containing $5\times10^7$ cells per ml. On each occasion, 0.1 ml of the cell suspension was subcutaneously implanted into the right axilla of a male mouse (ddY strain; body weight $20\pm2$ g). The test compound was dissolved in a physiological solution of sodium chloride with or without addition of Tween 80 and was administered intraperitoneally into each mouse of a group consisting of 5 mice at a dose of 0.1–0.2 ml, 24 hours after the implantation of the tumor cells.

The anti-tumor activity was determined in the following manner. 7 days after the implantation, the major axis (a) and the minor axis (b) of the tumor were measured to calculate a value of "$a\times b^2/2$" which corresponds to the volume of the tumor. The anti-tumor activity was expressed by the ratio of the volume of the tumors (T) of the group of animals administered with the test compound to the corresponding volume of tumors (C) of the untreated animals.

(2) Determination of $ED_{50}$:

$ED_{50}$ shows the amount of a substance needed for reducing the volume of Sarcoma 180 solid tumors in mice to 50% on the basis of the corresponding volume of Sarcoma solid tumors in control animals.

On graph paper, T/C (the ratio of the volume of tumors of treated animals to that of control animals) was indicated by an arithmetic scale on the longitudinal axis and the administered amount of the test compound was indicated by a logarithmic scale on the lateral axis. The relationship between the dose and T/C was shown by a straight line determined by the method of least squares, from which a dose corresponding to T/C of 0.5 was obtained.

(3) Acute toxicity:

Each animal of the test group consisting of 5 ddY mice was administered intraperitoneally once with a test compound. After this, the animals were observed for 14 days and deaths were noted. The $LD_{50}$ was determined by Beherns Kaerber's method.

(4) Effect on the peripheral leucocytes number:

Sarcoma 180 solid tumor cells ($5\times10^6$) were subcutaneously implanted into the right axilla of each mouse (body weight $20\pm2$ g) of a group consisting of 5 male mice (ddY strain). 24 hours after implantation, a test compound was intraperitoneally administered to each animal. 4 days later, blood (each 0.02 ml) was collected from the suborbital plexus vein of each tumor-carrying animal. The collected sample of blood was dispersed in 9.98 ml of Cell-Kit Seven solution. One drop of saponin solution was added to the sample to dissolve erythrocytes and then a microcell counter was used to count the number of leucocytes. On graph paper, the number of leucocytes was indicated on the y-axis by an arithmetic scale and the dose of the test compound was indicated on the x-axis by a logarithmic scale. The relationship between the number of peripheral leucocytes and the dosage of the test compound was plotted and the dosage corresponding to 4000 peripheral leucocytes/$mm^3$ (about half the number of leucocytes of normal mice) was obtained. This value is denoted in Table 2 by $WBC_{4000}$.

EXAMPLE 9

Anti-tumor activity against leukemia P-388

Ascites was sampled from the abdominal cavity of tumor-bearing mice (DBA/2) 7 days after transplantation of P-388 ascitic tumor. The number of the P-388 cells in the ascites was counted. A suspension of the tumor cells of $5\times10^6$/ml was prepared using sterilized physiological saline, and 0.2 ml of the suspension (containing $1\times10^6$ cells) was intraperitoneally transplanted to $CDF_1$ mice weighing 20 to 25 g. Twenty-four hours after the transplantation of the tumor, a test compound was intraperitoneally administered once to groups of the $CDF_1$ mice, each group consisting of 6 mice. Survival state was observed for 33 days. The effect of the compound was evaluated by a ratio of a mean survival days of the group treated with the compound to a mean survival days of the control group (untreated group) after 33 days of observation (Increased Life Span, ILS %). The results are shown in Table 3. Further, similar experiments were conducted using P-388 resistant to mitomycin C and the results are shown in Table 4. From Tables 3 and 4, it is evident that the maximum increased life span of Compound 3a was 213% and 143%, respectively, and that Compound 3a has more excellent anti-tumor activity than Compound A (its synthesis is shown in Reference Example) which exhibited the maximum increased life span of 75% and 73%. Therefore, it can be expected that Compound 3a would exhibit clinical effects superior to Compound A. In a similar experiment, ILS of Compound 1 at a dose of 10 mg/kg was 83%.

TABLE 3

| | Effect on P-388 leukemia (ILS %) | |
|---|---|---|
| Dose (mg/kg) | Compound 3a | Compound A |
| 0.0625 | — | 15 |
| 0.125 | — | 48 |
| 0.25 | 28 | 45 |
| 0.5 | 53 | 63 |
| 1.0 | 58 | 68 |
| 2.0 | 58 | 75 |
| 4.0 | 145 | 20 |
| 6.0 | 213 | — |
| 8.0 | 98 | — |

TABLE 4

| | Effect on P-388 leukemia resistant to mitomycin C (ILS %) | |
|---|---|---|
| Dose (mg/kg) | Compound 3a | Compound A |
| 0.25 | — | 47 |
| 0.5 | — | 73 |
| 1.0 | 28 | 68 |
| 2.0 | 103 | 47 |
| 4.0 | 143 | −41 |
| 6.0 | 58 | −47 |
| 8.0 | 51 | — |

EXAMPLE 10

3 g of Compound 3a is dissolved in 1000 ml of distilled water. The solution is sterilized by the use of a Millipore filter (pore size: 0.22μ) under pressure. The sterile filtrate is divided into fractions and poured into brown vials (1.0 ml per vial; 3 mg of active principle per vial). The vials are frozen at −50° C. for 2 hours, and a primary drying is effected in vacuo (0.1 mmHg) for 24 hours at a rack temperature of −10° C. After confirming that the rack temperature is the same as the material temperature, a secondary drying is effected in vacuo (0.1 mmHg) for 4 hours at a rack temperature of 30° C. to remove moisture. Each vial is then sealed with a rubber stopper. In use, 5 ml of a sterilized physiological solution of sodium chloride is poured into each vial. The vial is shaken to dissolve the ingredient. In this manner, an injectable preparation is prepared.

REFERENCE EXAMPLE

7-N-Dimethylaminomethylenemitomycin C
(Compound A; compound described in GB 2121796A, Example 8)

Compound A is obtained by the same procedures as in Example 3 except that mitomycin C is used as a starting compound.

$^1$H-NMR (CDCl$_3$): δ1.93(3H, s), 2.80(1H, dd, J=4.4, 2.0), 2.90(1H, d, J=4.4), 3.04(3H, s), 3.08(3H, s), 3.22(3H, s), 3.50(1H, dd, J=12.7, 2.0), 3.61(1H, dd, J=10.5, 4.4), 4.20(1H, d, J=12.7), 4.50(1H, dd, J=10.7, 10.5), 4.74(2H, br.), 4.78(1H, dd, J=10.7, 4.4), 7.69(1H, s).

IR (KBr): 3310, 2940, 1718, 1624, 1540, 1306, 1059 cm$^{-1}$.

MS (m/z): 389(M+), 357, 346, 328, 313, 297.

High resolution MS: M+=389.1720 (calcd. for C$_{18}$H$_{23}$N$_5$O$_5$=389.1697).

TLC (CHCl$_3$—MeOH, 9:1 v/v): Rf=0.40.

What is claimed is:

1. A mitomycin compound represented by the formula:

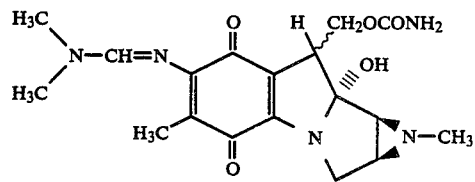

wherein ∼∼∼ represents α-bond.

* * * * *

UNITED STATES PATENT AND TRADEMARK OFFICE
CERTIFICATE OF CORRECTION

PATENT NO. : 4,748,251
DATED : May 31, 1988
INVENTOR(S) : KUNIKATSU SHIRAHATA, ET AL.

It is certified that error appears in the above-identified patent and that said Letters Patent is hereby corrected as shown below:

COLUMN 2

Lines 60-68, that part of the formula reading:

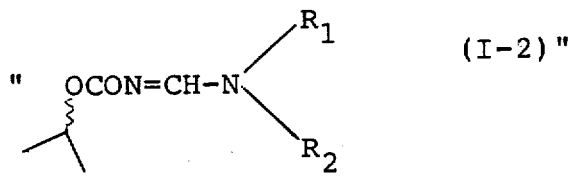

should read

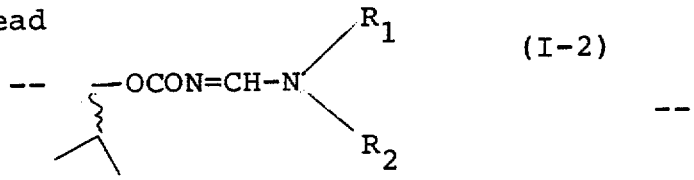

COLUMN 5

Lines 48-50, that part of the formula reading:

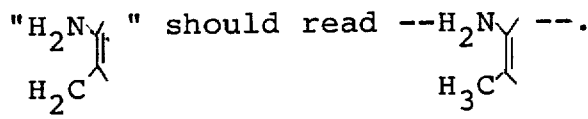

UNITED STATES PATENT AND TRADEMARK OFFICE
CERTIFICATE OF CORRECTION

PATENT NO. : 4,748,251

DATED : May 31, 1988

INVENTOR(S) : KUNIKATSU SHIRAHATA, ET AL.

It is certified that error appears in the above-identified patent and that said Letters Patent is hereby corrected as shown below:

COLUMN 9

Line 15, "1a-Demethyl-7-N-dimethylaminoethylenemitomycin G"

should read:

--1a-Demethyl-7-N-dimethylaminomethylenemitomycin G--.

Signed and Sealed this

First Day of November, 1988

Attest:

DONALD J. QUIGG

*Attesting Officer*    *Commissioner of Patents and Trademarks*